United States Patent [19]

Protasi et al.

[11] Patent Number: 5,284,937
[45] Date of Patent: Feb. 8, 1994

[54] PROCESS FOR THE EXTRACTION AND PURIFICATION OF HUMAN RECOMBINANT GAMMA INTERFERON

[75] Inventors: Otello Protasi; Donatella Mannucci, both of Siena, Italy

[73] Assignee: Sclavo S.p.A., Siena, Italy

[21] Appl. No.: 734,778

[22] Filed: Jul. 23, 1991

[30] Foreign Application Priority Data

Jul. 25, 1990 [IT] Italy ................. 21051 A/90

[51] Int. Cl.$^5$ ............... A61K 37/66; C07K 3/12; C07K 15/26
[52] U.S. Cl. .................. 530/351; 424/85.5; 435/69.51; 530/423; 530/427
[58] Field of Search ............ 530/351, 423, 427; 435/69.51; 424/85.5

[56] References Cited

U.S. PATENT DOCUMENTS

| | | | |
|---|---|---|---|
| 4,511,502 | 4/1985 | Builder et al. | 435/69.51 |
| 4,511,503 | 4/1985 | Olson et al. | 530/351 |
| 4,599,197 | 7/1986 | Wetzel | 435/69.1 |
| 4,620,948 | 11/1986 | Builder et al. | 435/69.51 |
| 4,681,930 | 7/1987 | Kung et al. | 530/351 |
| 4,751,078 | 6/1988 | Nagabhushan et al. | 530/351 |
| 4,828,989 | 5/1989 | Prior et al. | 530/351 |
| 4,828,990 | 5/1989 | Higashi et al. | 530/351 |
| 4,874,697 | 10/1989 | Sugimura et al. | 435/69.51 |
| 4,908,432 | 3/1990 | Yip | 424/85.5 |

FOREIGN PATENT DOCUMENTS

8904177  5/1989  World Int. Prop. O. .

OTHER PUBLICATIONS

*Protein Purification Methods,* Harris et al., Eds. IRL Press. 1989, pp. 88,92.

*Primary Examiner*—Jeffrey E. Russel
*Attorney, Agent, or Firm*—Birch, Stewart, Kolasch & Birch

[57] ABSTRACT

An extraction and purification process for human gamma interferon (HuIFN-gamma) from recombinant host cells producing the same in insoluble form is described, which comprises suspending the cells in a buffer solution having pH from 6.0 to 8.5, optionally complemented with an osmoprotector; disrupting the cells in conditions which do not activate the endocellular proteases; separating and solubilizing the pellet containing the insoluble HuIFN-gamma by extraction with phosphate buffer having pH comprised between 6.5 and 8.5 and finally purifying the solubilized HuIFN-gamma by one or more chromatographic techniques. Such a process allows non-degraded HuIFN-gamma to be obtained, with a biological activity and chemical-physical properties unaffected vis-a-vis the native product and in high yield and purity.

10 Claims, No Drawings

PROCESS FOR THE EXTRACTION AND PURIFICATION OF HUMAN RECOMBINANT GAMMA INTERFERON

The present invention relates to a process for the extraction and purification of human gamma-interferon from host cells transformed with recombinant DNA techniques and which produce the same in insoluble form. The present invention also relates to the use of the same for manufacturing pharmaceutical compositions suitable as antivirals, antitumorals and immunomodulators.

The interferons, briefly designated IFN, are glycoprotein substances which are produced by different animal or human cells (fibroblasts, leucocytes and lymphocytes) as a response to viral and nonviral agents during the first phases of an infection.

At present at least three types of interferon have been identified and characterized (alpha, beta, gamma), which differ from each other both for antigenic properties and biological activity.

In particular the human gamma-interferon (HuIFN-gamma) is an acid labile glycoprotein with molecular weight about 34,000 daltons and produced by leucocytes.

HuIFN-gamma exhibits, in addition to an antiviral and immunomodulator activity, an antitumor activity capable of inducing an in vivo regression of a tumor.

Therefore HuIFN-gamma is particularly suitable as an active agent for manufacturing pharmaceutical compositions useful as antivirals, antitumorals and immunomodulators. There is described in the prior art the production of human gamma-interferon in vitro by leucocytes in culture or by fermentation methods of host cells transformed with recombinant DNA techniques (see for example the EP-A-88 540).

Said methods, though enabling an improved yield in polypeptide production with regard to the in vitro techniques, are not free of important purification problems.

In fact the synthesis of redundant heterologous proteins or polypeptides, where heterologous indicates compound not naturally produced by the host cells, may affect the viability of the cells. Therefore sometimes the host organism provides a biological mechanism (proteolytic degradation or secretion) which allows the host cell to prevent interactions of the heterologous protein with the essential metabolic processes of the cell.

As a further option, for the product of heterologous gene expression may be produced in an altered conformation which limits its interference with the normal cellular pathways. In fact such heterologous products have been often observed in host organisms like *E. coli* or *S. cerevisiae* to be produced in non-native forms and to precipitate within the cells, forming protein aggregates known as "inclusion bodies" or "refractory bodies." Generally a process for isolating and purifying recombinant products (proteins or polypeptides) giving rise to insoluble aggregates within the host cells comprises disrupting said cells by means of conventional techniques to extract said aggregates, separating the cellular fragments from the supernatant containing said aggregates (which form a pellet) by filtration or centrifugation, solubilizing the pellet and purifying the solubilized recombinant product.

Methods for the purification of insoluble recombinant products, in particular of recombinant human gamma-interferon are known in the prior technique, which are essentially based on the use of denaturing agents like urea or guanidinium chloride for solubilizing the protein aggregates and on the use of substances intended to inhibit the endocellular proteases, activated during the breakage of the cell, to avoid the proteolytic degradation of the recombinant products.

By way of example of U.S. Pat. Nos. 4,511,502 and 4,620,948 disclose processes for the purification of insoluble heterologous proteins inter alia gamma-interferon, wherein the aggregate solubilization is carried out by means of a denaturing agent, preferably 9M guanidinium chloride or thiocyanate salts in presence of a detergent (0.01–0.02%) or of a reducing agent like β-mercaptoethanol.

Said methods however exhibit the following drawbacks:
production of soluble denatured products, thus products having a folding and a biological activity considerably different from those of the native products, which therefore need to be reactivated before the use;
incomplete reactivation of the denatured products by means of known techniques such as e.g. that disclosed in the U.S. Pat. No. 4,599,197;
activation of the endocellular proteases during the cell disruption phase;
unsatisfactory production yields in solubilized product (about 30–40%) due to a partial reaggregation during the chromatographic purification, the eluting being carried out in absence of denaturing agents.

An improvement in yield may be obtained by applying in the final elution a denaturing agent; however the resulting product would not be suitable for use as such because of the presence of said denaturing agent.

In order to prevent the enzymatic degradation, the U.S. Pat. No. 4,681,930 describes a method for the purification of recombinant gamma-interferon based on the use of cellular enzymatic protease inhibitors.

The use of such inhibitors, either alone or in combination with a solubilizing agent, does not allow the recombinant products with the desired features to be obtained.

In fact, though the endocellular protease catalyzed enzymatic degradation of the polypeptide is inhibited, an insoluble denatured product is nevertheless obtained.

For such reasons there are proposed in the prior art other purification methods for insoluble human gamma-interferon isolated from recombinant cells.

Said methods are based on the use of zinc or copper salts or polyethylenimine salts (WO 86/04067) or on the sequential removal of nucleic acids, of contaminating proteins and other contaminating substances of different molecular weights by means of different chromatographic techniques (U.S. Pat. No. 4,751,078). All of those cited methods are not yet fully satisfactory either because of the low production yields (WO 86/04067) or because of the number of necessary stages (U.S. Pat. No. 4,751,078).

In conclusion, despite of the great deal of performed works, no system turned out to be suitable for the preparation of a product satisfactory for a therapeutic application and, at the same time, convenient to allow an industrial scale up.

It has now been found that the shortcomings of the prior art may be avoided with a process based essentially on the use of nondenaturing agents for the solubilization of the pellet comprising the insoluble interferon-gamma.

Such a process enables the production of interferon-gamma, with unimpaired biological activity and unchanged chemical-physical properties, in high yield (65-75%) and purity, expressed as specific activity, of $1 \times 10^8$ International Units per mg protein (IU/mg). Therefore an object of the present invention is a process for the extraction and purification of human interferon-gamma from recombinant host cells producing the same in insoluble form. A further object of the present invention is an essentially pure polypeptide having biological activity and chemical-physical properties of the native human gamma-interferon obtained with the aforementioned process.

Still further objects of the present invention are pharmaceutical compositions suitable as antivirals, antitumorals and immunomodulators comprising a therapeutically effective amount of human gamma-interferon obtained with the process of the present invention.

Other objects of the present invention will be evident from the description and examples which follow.

In detail, the extraction and purification process of the present invention comprises:

a) suspending the recombinant host cells which produce human gamma-interferon in the form of insoluble aggregates in a buffer solution having pH comprised between 6.0 and 8.5, optionally complemented with an osmoprotector and disrupting the cells in conditions which do not activate the endocellular proteases;

b) separating the suspension of protein aggregates (pellet) which contain gamma-interferon from the cell debris produced in stage (a);

c) separating the pellet containing the insoluble recombinant human gamma-interferon from the supernatant;

d) solubilizing the recombinant human gamma-interferon by one or more extractions of the pellet with phosphate buffer having pH comprised between 6.5 and 8.5;

e) purifying gamma-interferon by means of one or more chromatographic techniques.

As for the gamma-interferon to be purified, it can be obtained from host cells, such as *Escherichia coli* or *Saccharomyces cerevisiae*, transformed with an expression vector containing the gene encoding the gamma-IFN as disclosed by e.g. E. Erhard and C. P. Hollenberg, (1983), Journal of Bacteriology, 156:625-635).

The cells recovered from the culture medium by means of centrifugation or filtration, are broken applying conventional techniques, e.g. osmotic shock, sonication, milling or chemical agents, in order to isolate the insoluble aggregates.

According to a preferred embodiment of the present invention, the cells are disrupted by homogenization in a bead-disrupter mill using commercial equipment.

In particular the cells are repeatedly washed with at least 30 volumes of buffer having a pH from 6.0 to 8.5. Thereafter they are suspended in the same washing buffer, optionally inpresence of an osmoprotector such as e.g. sorbitol at a concentration (weight/volume) comprised between 20% and 30%, preferably between 23% and 28%.

Buffers suitable for the purpose of the present invention are for instance Tris-HCl and phosphate buffer SORENSEN.

According to the present invention the homogenization is carried out in conditions suitable to obtain a high rate of cell breakage (98-99%), which is necessary to release the HuIFN-gamma-containing protein aggregates, without however collapsing the lysosomal vacuoles containing the enzymatic proteases. Disruption of the lysosomes would cause proteolytic degradation of the HuIFN-gamma. The homogenization is preferably carried out using lead-free glass beads having diameter from 0.25 to 0.5 mm with a rotation speed of the dishes from 2,000 to 4,000 revolutions per minute (rpm), preferably from 2,700 to 3,500, more preferably the speed is 3,000 rpm, i.e. 10 meters/second, for a period of time for 45 seconds to 2 minutes, preferably for one or about one minute. In fact, experimentation concerning the length of the homogenization time shows, see Table 1, that one minute homogenization is suitable to obtain a high percent rate of cell breakage, while avoiding the proteolysis problems which arise from prolonged homogenizations.

Finally the homogenate is recovered and added to the washes of the milling vessel made with the same buffer. The homogenate is then decanted and centrifuged first at a speed between 2,000 and 5,000 rpm, preferably between 3,500 and 4,500 rpm, with the purpose of separating the suspension of the gamma-interferon- comprising protein aggregates (pellet) from the cell debris and from the remaining glass beads and following at a speed about 100,000 rpm to sediment the aggregates which are thereafter removed from the supernatant. The so obtained pellet is repeatedly washed with the same homogenization buffer to completely eliminate the still present lipidic residues; said residues in fact could give rise to clarity problems in the following extractions, and cause obstruction of the adaptor membranes of the chromatographic column with resulting flow hindrance. The pellet is thereafter solubilized upon one or more extractions with phosphate buffer of pH comprised between 6.4 and 8.5, preferably 7.5 and 8.0, using a pellet/buffer ratio (weight/volume) from 2 to 20% preferably from 5 to 10%.

The extraction is accomplished at temperature comprised from 0° C. to 25° C., preferably from 4° C. for a period of 10 to 30 hours, preferably 15 to 20 hours. Buffers suitable for the purposes of the present invention are Tris-HCl and, preferably phosphate buffer SORENSEN prepared by mixing different amounts of the solutions A and B comprising respectively $KH_2PO_4$, 9.08 g/l and $Na_2HPO_4 \times 2H_2O$), 11.88 g/l. The purification of recombinant human gamma-interferon solubilized according to the process of the present invention may be achieved with one or more conventional chromatographic techniques, such as, e.g. ion exchange chromatography and/or hydrophobic chromatography. Preferably said purification is carried out with ion exchange chromatography. It was in fact observed that the isoelectric point (PI) of the recombinant human gamma interferon, solubilized according to the process of the present invention has a value lower than 8 unlike the product obtained with denaturing agents which has a PI>8. The combined mechanical disruption of the cells (homogenization) under the aforementioned conditions with the phosphate buffer, pH 6.5-8.5 extraction, enable a non-denatured, non-degraded product to be obtained in high final yield and purity, expressed as specific activity, of about $1 \times 10^8$ International Units/mg (IU/mg).

The experimental examples which follow are intended to illustrate, but not however to limit, the present invention.

EXAMPLE 1

Effect of the homogenization time on cellular protease activation

S. cerevisiae cells capable of expressing recombinant human gamma-interferon in insoluble form and recovered from a fermentation run in a bioreactor, are washed twice, 5 minutes/wash, with 30 volumes phosphate buffer SORENSEN, pH 6.8 complemented with 1M sorbitol as an osmoprotector.

The cells (about 17 g wet biomass, corresponding to from $4.16 \times 10^9$ cells/ml) are suspended in 64 ml SORENSEN buffer, pH 6.8 complemented with sorbitol and transferred into a DYNO-MILL homogenizer type KLD equipped for discontinuous running as follows:
- unleaded glass milling vessel, 0.15 liters;
- VULCOLLAN stirring discs (64 mm diameter);
- cooling by means of a refrigerator block (rectified glycol) for thermostated temperature within the milling vessel at 8° C.;
- unleaded glass beads of 0.25-0.50 mm diameter in amount of 125 ml;
- rotation speed of the disks 3,000 rpm, i.e. 10 meter/second.

The cell breakage rate and the corresponding enzymatic degradation are determined, at different homogenization times, by cell count per milliliter and by sodium dodecylsulfate polyacrylamide gel electrophoresis analysis (SDS PAGE) of the proteins present in the supernatant after separation of the products of the cell lysis.

The results are reported in Table 1

TABLE 1

| Homogen. time | yeast cell/ml | cell/ml after homog. | % breakage |
|---|---|---|---|
| 45" | $7.02 \times 10^9$ | $1.05 \times 10^9$ | 85.0 |
| 1' | $7.66 \times 10^9$ | $1.20 \times 10^8$ | 98.4 |
| 1' 30" | $4.16 \times 10^9$ | $4.58 \times 10^6$ | 98.8 |
| 2' | $5.07 \times 10^9$ | $1.12 \times 10^7$ | 99.7 |

From such figures it can be appreciated that 1 minute homogenization is sufficient to obtain a high rate of cell breakage, while avoiding the proteolysis drawbacks raised by longer homogenization times.

EXAMPLE 2

Analysis of the pH effect on the pellet solubilization

S. cerevisiae cells are homogenized for one minute as described in example 1. The homogenate and the washes with SORENSEN buffer of the milling vessel are recovered and transferred into a glass vessel and decanted to separate the glass beads.

Thereafter the suspension of the protein aggregates which comprise the gamma-interferon is separated from the cell debris and from the still remaining glass beads by centrifugation at 4° C. for 10 minutes at 4,000 rpm with a Heraeus Mini Fuge T centrifuge.

The obtained suspension is further centrifuged at 4° C. for 60 minutes (Beckman L8-M centrifuge 100,000 rpm) to sediment the pellet of protein aggregates.

Thereafter the pellet is separated from the supernatant by decanting and washed twice with about 10 ml phosphate buffer SORENSEN, pH 6.8 to completely eliminate the lipidic residues present upon the pellet and the walls of the centrifuge tube. The aggregates containing the gamma-interferon are then solubilized by extraction of the pellet in phosphate buffer SORENSEN, at varying pH values. The extraction is actually carried out by suspending the pellet (about 1 g) having an activity of $3.9 \times 10^6$ IU/ml in 20 ml buffer and maintaining the resulting suspension at 4° C. for 20 hours with stirring.

The gamma-interferon present in the extract and in the remaining pellet is determined with an essay for antiviral activity after separation by 100,000 rpm centrifugation for 10 minutes. It can be appreciated from the results reported in Table 2 that the highest solubilization effectiveness is obtained at pH 8.0 and 7.6.

TABLE 2

| Test | IU/ml |
|---|---|
| Extract pH 8.0 | 108 000 |
| Extract pH 7.6 | 101 000 |
| Extract pH 7.0 | 8 000 |
| Extract pH 6.6 | 9 600 |
| Extract pH 6.0 | 14 000 |
| Extract pH 5.6 | 9 600 |
| Extract pH 5.0 | 9 000 |
| Pellet pH 8.0 | 480 000 |
| Pellet pH 7.6 | 672 000 |
| Pellet pH 7.0 | 720 000 |
| Pellet pH 6.6 | 720 000 |
| Pellet pH 6.0 | 768 000 |
| Pellet pH 5.6 | 864 000 |
| Pellet pH 5.0 | 1 008 000 |

EXAMPLE 3

Extraction with buffer SORENSEN pH 8.0

The process is carried out in the same manner as in preceding example 2, using SORENSEN buffer, pH 8.0 complemented with 1M sorbitol, in the homogenization phase. After separation of the supernatant (60 ml) with centrifugation at 100,000 rpm, the pellet (comprising 1,874,000 IU/ml gamma-interferon) is extracted three times with 90 ml buffer for a period of time of 24 hours. The results reported in Table 3 show that about 65% of gamma-interferon contained by the aggregates is solubilized upon extraction at pH 8.0.

TABLE 3

| Test | IU/ml | mg/ml | IU/mg | tot. ml | tot IU |
|---|---|---|---|---|---|
| a) | $1.536 \times 10^3$ | 6.87 | $2.2 \times 10^5$ | 60 | $9.20 \times 10^7$ |
| b) | $1.874 \times 10^3$ | — | — | 56 | $1.05 \times 10^8$ |
| c) | 247 700 | 0.356 | $6.9 \times 10^5$ | 90 | $2.20 \times 10^7$ |
| d) | 365 400 | 0.47 | $7.7 \times 10^5$ | 90 | $3.30 \times 10^7$ |
| e) | 130 000 | 0.167 | $7.7 \times 10^5$ | 90 | $1.20 \times 10^7$ |
| f) | 380 000 | — | — | 56 | $2.00 \times 10^7$ |
| g) | 207 250 | 0.298 | $7.0 \times 10^5$ | 270 | $5.60 \times 10^7$ | where:
a) is supernatant obtained after centrifugation at 100,000 rpm;
b) is the suspension of the pallet of aggregates in buffer SORENSEN pH 8.0;
c) is the first extract in buffer SORENSEN pH 8.0; d) is the second extract in buffer SORENSEN pH 8.0;
e) is the third extract in buffer SORENSEN pH 8.0;
f) is the pellet residue and
g) is the pool of extracts.

EXAMPLE 4

Purification of the solubilized gamma-interferon by cation exchange chromatography A chromatography column Pharmacia C-16 is used, which contains 1 ml of SP-Sephadex® resin (cation exchanger) equilibrated with 0.05M NaCl in SORENSEN buffer pH 8.0.

The column is loaded with 135 ml of the pool of the extracts obtained according to example 3 having a gamma-interferon titre of $2.8 \times 10^7$ total IU.

After loading, the column is eluted with 100 ml buffer having the aforementioned composition and the eluate is analyzed by assaying the antiviral activity to determine the presence, if any, of gamma-interferon. The results reported in Table 4 show that the eluate comprises the total amount of loaded interferon, proving that by such operative conditions the recombinant gamma-interferon is not bound to the resin.

TABLE 4

| Test | IU/ml | mg/ml | IU/mg | tot. ml | tot IU |
|---|---|---|---|---|---|
| a) | $1.536 \times 10^3$ | 6.87 | $2.2 \times 10^5$ | 60 | $9.20 \times 10^7$ |
| b) | $1.874 \times 10^3$ | — | — | 56 | $1.05 \times 10^8$ |
| c) | 207 250 | 0.298 | $7.0 \times 10^5$ | 135 | $2.80 \times 10^7$ |
| d) | 238 620 | 0.286 | $8.3 \times 10^5$ | 135 | $3.20 \times 10^7$ | where:
a) is the supernatant obtained after centrifugation at 100,000 rpm;
b) is the suspension of the pellet of aggregates in SORENSEN buffer pH 8.0;
c) is the pool of the loaded extracts and
d) the eluted pool.

EXAMPLE 5

Purification of the solubilized gamma-interferon by anion exchange chromatography The process is carried out in the same manner as in example 4, but using 12 ml of Sepharose-Q ® resin (anion exchanger) equilibrated with 0.05M NaCl in SORENSEN buffer pH 8.0.

After loading, the column is eluted with 100 ml buffer having the aforementioned composition and the eluate [test (b)] is analyzed by assaying the antiviral activity.

The absence of gamma-interferon shows that this is bound to the anion exchanger. The gamma-interferon is thereafter eluted from the column with a NaCl gradient (from 0.05 to 0.5M); the different fractions are collected and submitted to gamma-interferon determination.

The results reported in table 5 show that the fractions 2 to 5 contain gamma-interferon having a specific activity, of $1.05 \times 10^8$ IU/mg and in yield of 75%.

Said results indicate that the isoelectric point (PI) of gamma-interferon solubilized with SORENSEN buffer pH 8.0, without using denaturing agents, is lower than 8.0 unlike the product obtained by urea extraction, which has PI higher than 8.0 on SP-Sephadex ®.

| (NaCl 0.5M) | | | | | |
|---|---|---|---|---|---|
| F122 | $1.40 \times 10^5$ | 0.013 | $3.07 \times 10^6$ | 10 | $1.40 \times 10^6$ |
| F123 | $1.18 \times 10^5$ | 0.023 | $7.80 \times 10^5$ | 10 | $1.18 \times 10^6$ |
| F124 | $9.90 \times 10^4$ | 0.022 | $4.30 \times 10^4$ | 10 | $9.90 \times 10^5$ |
| F125 | $5.76 \times 10^4$ | 0.024 | $2.60 \times 10^4$ | 10 | $5.76 \times 10^5$ |
| (NaCl 0.5M + Urea 6M) | | | | | |

TABLE 5

| Test | IU/ml | mg/ml | IU/mg | tot. ml | tot IU |
|---|---|---|---|---|---|
| a) | 207,250 | 0.298 | $7.00 \times 10^5$ | 135 | $2.80 \times 10^7$ |
| b) | 18,600 | 0.051 | $3.60 \times 10^5$ | 135 | $2.50 \times 10^6$ |
| c) | 8,500 | 0.007 | $1.20 \times 10^6$ | 5 | $4.20 \times 10^4$ |
| d) | $1,050 \times 10^3$ | 0.01 | $1.05 \times 10^8$ | 20 | $2.10 \times 10^7$ |
| e) | 8,300 | 0.038 | $2.20 \times 10^5$ | 100 | $8.30 \times 10^5$ |
| f) | 136,600 | 0.027 | $5.00 \times 10^6$ | 15 | $2.00 \times 10^6$ |
| g) | 71,200 | 0.029 | $2.45 \times 10^6$ | 15 | $1.06 \times 10^6$ |
| h) | 47,000 | 0.061 | $7.70 \times 10^5$ | 10 | $4.70 \times 10^5$ | where:
a) is the pool of loaded extracts;
b) pool of eluates;
c) fraction 1;
d) fractions 2 to 5 (NaCl 0.08M);
e) fractions 6 to 25;
f) fractions 26 to 28 (NaCl 0.23M);
g) fractions 29 to 31 (NaCl 0.32M);
h) fractions 32 to 33 (NaCl 0.50M).

EXAMPLE 6

Extraction and purification of human recombinant gamma-interferon with denaturing agents (comparison)

The pellet of aggregates obtained according to example 1, is suspended in 80 ml 0.025M Tris-HCl buffer, 1 mM EDTA, 6M urea, pH 8.0 and the resulting suspension is extracted at 4° C. for one night with gentle stirring.

The suspension is then centrifuged at 100,000 rpm for 60 minutes at 4° C. to separate the remaining pellet from the supernatant containing the solubilized gamma-interferon. Said supernatant, which is not completely clear, is purified on cation exchange chromatography using a Pharmacia K 50/30 chromatography column packed with 25 ml SP-Sephadex ® C50 equilibrated with 0.025M Tris-HCl buffer, 1 mM EDTA, pH 8.0 at 4° C. The column is fed with the extract at a flow rate of 100 ml/hour. After the loading, the column is washed with the same equilibration buffer (500 ml) fed at flow rate of 30 ml/hour until completely urea-free eluate is collected (monitored with enzymatic assay using the Kit Sclavo). Then a first elution from the column of human recombinant gamma-interferon is carried out by applying a gradient from 0.025M Tris-HCl buffer, 1 mM EDTA, 0.05M NaCl, pH 8.0 to 0.025M Tris-HCl buffer, 1 mM EDTA, 0.5M NaCl., pH 8.0 and at a flow rate of 100 ml/hour. Programmed time for the gradient: 1 hour.

Finally the column is eluted with 0.025M Tris-HCl buffer, 1 mM-EDTA, 0.5M NaCl and 6M Urea, pH 8.0. The eluted fractions are collected and screened to determined the antiviral activity. The results are reported in table 6.

TABLE 6

| Test | IU/ml | mg/ml | IU/mg | tot. ml | tot IU |
|---|---|---|---|---|---|
| Load | $3.89 \times 10^5$ | 0.395 | $9.80 \times 10^5$ | 80 | $3.10 \times 10^7$ |
| Washes | <9 000 | 0.17 | — | 80 | — |
| F1–F16 | <9 000 | — | — | 150 | — |
| (NaCl 0.3M) | | | | | |
| F17 | $1.27 \times 10^5$ | 0.010 | $1.27 \times 10^7$ | 12 | $1.52 \times 10^6$ |
| F18 | $1.22 \times 10^5$ | 0.012 | $1.02 \times 10^7$ | 8 | $9.80 \times 10^5$ |
| F19 | $2.90 \times 10^5$ | 0.012 | $2.40 \times 10^7$ | 7 | $2.00 \times 10^6$ |
| F20 | $3.15 \times 10^5$ | 0.010 | $3.10 \times 10^7$ | 5 | $1.57 \times 10^6$ |
| F21 | $3.90 \times 10^5$ | 0.009 | $4.30 \times 10^7$ | 7 | $2.70 \times 10^6$ |
| F22 | $2.18 \times 10^5$ | 0.010 | $2.20 \times 10^7$ | 8 | $1.74 \times 10^6$ |
| F23 | $1.74 \times 10^5$ | 0.010 | $1.70 \times 10^7$ | 8 | $1.40 \times 10^6$ |
| F24 | $1.36 \times 10^5$ | 0.008 | $1.70 \times 10^7$ | 12 | $1.63 \times 10^6$ |
| F25–35 | <9 000 | — | — | 100 | — |
| (NaCl 0.5M + Urea 6M) | | | | | |
| F36 | $6.36 \times 10^5$ | 0.163 | $3.80 \times 10^6$ | 7 | $4.40 \times 10^6$ |
| F37 | $2.78 \times 10^5$ | 0.063 | $4.30 \times 10^6$ | 7 | $1.90 \times 10^6$ |
| F38 | $1.90 \times 10^5$ | 0.053 | $3.60 \times 10^6$ | 7 | $1.30 \times 10^6$ |
| F39 | $1.80 \times 10^5$ | 0.031 | $5.80 \times 10^6$ | 12 | $2.10 \times 10^6$ |

It can be appreciated from the above figures that:

the elution with a salt gradient without urea at a NaCl concentration of 0.3M allows human recombinant gamma-interferon to be obtained in sufficient purity (specific activity $4.3 \times 10^7$ IU/mg) and with the yield of about 45%;

the subsequent treatment of the column with urea-containing buffer allow the elution of that part of gamma-interferon which has likely become segregated after washing the column with urea-free buffer and which has specific activity $4.3 \times 10^6$ IU/mg; and with the yield of about 45%;

the pellet remaining after such an extraction still exhibits a content of human recombinant gamma-interferon which can be estimated to be about 50% of to starting product.

COMPARATIVE EXAMPLE 7

The aggregate pellet obtained according to example 1, is suspended in 64 ml 0.025M Tris-HCl buffer, 1 mM EDTA, 6M urea, 0.05M NaCl, pH 8.0 and the resulting suspensions extracted at 4° C. for one night with gentle stirring. The suspensions then centrifuged at 100,000 rpm for 60 minutes at 4° C. to separate the remaining pellet from the supernatant containing the solubilized gamma-interferon.

The supernatant (57 ml) is loaded at a flow rate of 57 ml/hour (0.048 ml/minute × per cm²) onto a Pharmacia K 50/30 column packed with 100 ml SP-Sephadex ® C50 equilibrated with the same buffer. After loading, the column is washed with about 500 ml of 0.025M Tris-HCl buffer, 1 mM EDTA, 6M Urea, 0.05M NaCl, pH 8.0 and the amount of interferon in the eluate is determined. Then the elution from the column of human recombinant gamma-interferon is carried out at a flow rate of 100 ml/hour.

(0.084 ml/minute × cm²) with 0.025M Tris-HCl, 1 mM EDTA, containing increasing molarity of NaCl (0.075M, 0.1M, 0.2 M, 0.3M, 0.4M and 0.5M). Finally, the column is eluted with 0.025M Tris-HCl buffer, 1 mM EDTA, 6M urea, 0.5M NaCl, pH 8.0. The eluted fractions are collected and analysed to detect the presence of gamma-interferon. The results are reported in table 7.

TABLE 7

| Test | IU/ml | mg/ml | IU/mg | tot. ml | tot IU |
|---|---|---|---|---|---|
| Load | $5.10 \times 10^5$ | 1.417 | $3.6 \times 10^5$ | 57 | $2.9 \times 10^7$ |
| Eluate | 6.400 | 0.403 | — | 57 | — |
| F11–F15 | <640 | 0.018 | — | 50 | — |
| (NaCl 0.075M) | | | | | |
| F28–32 | <640 | 0.013 | — | 50 | — |
| (NaCl 0.1M) | | | | | |
| F48–52 | <640 | 0.032 | | 50 | |
| (NaCl 0.2M) | | | | | |
| F69 | $2.97 \times 10^5$ | 0.009 | $3.30 \times 10^7$ | 10 | $2.97 \times 10^6$ |
| F70 | $3.82 \times 10^5$ | 0.007 | $5.40 \times 10^7$ | 10 | $3.82 \times 10^6$ |
| F71 | $2.45 \times 10^5$ | 0.010 | $2.40 \times 10^7$ | 10 | $2.45 \times 10^6$ |
| F72 | $3.17 \times 10^5$ | 0.008 | $3.90 \times 10^7$ | 10 | $3.17 \times 10^6$ |
| F73 | $1.96 \times 10^5$ | 0.006 | $3.30 \times 10^7$ | 10 | $1.96 \times 10^6$ |
| (NaCl 0.3M) | | | | | |
| F88 | $2.30 \times 10^4$ | 0.020 | $1.16 \times 10^6$ | 10 | $2.30 \times 10^5$ |
| F89 | $5.10 \times 10^4$ | 0.021 | $2.40 \times 10^6$ | 10 | $5.10 \times 10^5$ |
| F90 | $3.00 \times 10^4$ | 0.022 | $1.36 \times 10^6$ | 10 | $3.00 \times 10^5$ |
| F91 | $1.40 \times 10^4$ | 0.021 | $6.80 \times 10^5$ | 10 | $1.40 \times 10^5$ |
| F92 | $9.10 \times 10^3$ | 0.018 | $5.00 \times 10^5$ | 10 | $9.10 \times 10^4$ |
| (NaCl 0.4M) | | | | | |
| F103–106 | <640 | 0.017 | — | 40 | — |

TABLE 7-continued

| Test | IU/ml | mg/ml | IU/mg | tot. ml | tot IU |
|---|---|---|---|---|---|
| (NaCl 0.5M) | | | | | |
| F122 | $1.40 \times 10^5$ | 0.013 | $3.07 \times 10^6$ | 10 | $1.40 \times 10^6$ |
| F123 | $1.18 \times 10^5$ | 0.023 | $7.80 \times 10^5$ | 10 | $1.18 \times 10^6$ |
| F124 | $9.90 \times 10^4$ | 0.022 | $4.30 \times 10^4$ | 10 | $9.90 \times 10^5$ |
| F125 | $5.76 \times 10^4$ | 0.024 | $2.60 \times 10^4$ | 10 | $5.76 \times 10^5$ |
| (NaCl 0.5M + Urea 6M) | | | | | |

From the above figures it can be derived that gamma-interferon of sufficient purity (specific activity of about $5.4 \times 10^7$ IU/mg) in yield of about 45% can be obtained upon elution with buffer comprising 0.3 NaCl. In this case too, the final elution with 6M Urea and 0.5M NaCl relates gamma interferon having specific activity of $3.07 \times 10^6$ IU/mg.

We claim:

1. Process for the extraction and purification of human gamma interferon from recombinant host cells producing the same in form of insoluble aggregates comprising:
   a) suspending the recombinant host cells producing the human gamma interferon in form of insoluble aggregates in a buffer solution having pH comprised between 6.0 and 8.5, optionally complemented with an osmoprotector and disrupting the cells;
   b) separating the supernatant comprising the insoluble aggregates from the cell debris obtained in stage (a);
   c) separating the pellet containing the aggregates of recombinant human gamma interferon from the supernatant;
   d) solubilizing the aggregates of recombinant human gamma interferon by one or more extractions of the pellet with a non-denaturing phosphate buffer having pH comprised between 6.5 and 8.5; and finally
   e) purifying the solubilized recombinant human gamma interferon by means of one or more chromatographic techniques.

2. Process according to claim 1, wherein the osmoprotector is sorbitol.

3. Process according to claim 1, wherein in stage (a) the cells are disrupted by homogenization at rotation speed comprised from 2,000 to 4,000 revolutions per minute for a period of time ranging from 45 seconds to 2 minutes.

4. Process according to claim 3, wherein the rotation speed is comprised from 2,700 to 3,500 revolutions per minutes.

5. Process according to claim 3, wherein the homogenization time is one, or about one minute.

6. Process according to claim 1, wherein the phosphate buffer is Tris-HCl buffer or SORENSEN buffer.

7. Process according to claim 1, wherein in stage (d) the phosphate buffer has pH comprised from 7.5 to 8.0.

8. Process according to claim 1, wherein in stage (e) the purification is carried out by anion exchange chromatography.

9. Human recombinant gamma-interferon obtained by the process according to claim 1, characterized by an isoelectric point lower than 8.

10. Pharmaceutical compositions suitable as antitumor, antiviral and immunomodulator comprising a therapeutically effective amount of human recombinant gamma interferon according to claim 9.

* * * * *